(12) United States Patent
Solazzo

(10) Patent No.: US 6,419,662 B1
(45) Date of Patent: Jul. 16, 2002

(54) CONTINUOUS IRRIGATION Y-TUBING CONTROL VALVE DEVICE AND SYSTEM

(76) Inventor: Anthony Solazzo, 904 Oak Tree Rd., South Plainfield, NJ (US) 07080

( * ) Notice: Subject to any disclaimer, the term of this patent is extended or adjusted under 35 U.S.C. 154(b) by 30 days.

(21) Appl. No.: 09/772,510

(22) Filed: Jan. 30, 2001

(51) Int. Cl.[7] .................................................. A61M 5/00
(52) U.S. Cl. ...................... 604/248; 604/247; 137/875; 137/448; 137/192
(58) Field of Search ................................. 604/248, 247, 604/246, 254, 256; 637/448, 411, 192, 202, 875

(56) References Cited

U.S. PATENT DOCUMENTS

| | | | | |
|---|---|---|---|---|
| 2,024,548 A | * | 12/1935 | Struve | 137/104 |
| 3,270,770 A | * | 9/1966 | Wilson | 137/434 |
| 3,356,460 A | * | 12/1967 | King et al. | 23/272 |
| 3,472,317 A | * | 10/1969 | Fowler | 166/5 |
| 3,584,642 A | * | 6/1971 | Robert | 137/270 |
| 3,599,711 A | * | 8/1971 | John | 166/5 |
| 3,605,780 A | * | 9/1971 | Kranz | 137/81.5 |
| 3,630,221 A | * | 12/1971 | Robert | 137/448 |
| 3,773,062 A | * | 11/1973 | McIver | 137/1 |
| 3,844,283 A | * | 10/1974 | Dabney | 128/214 |
| 4,324,238 A | * | 4/1982 | Genese et al. | 128/214 |
| 4,681,559 A | * | 7/1987 | Hooven | 604/9 |
| 4,718,457 A | * | 1/1988 | Luger | 137/875 |
| 4,730,638 A | * | 3/1988 | Hazelton | 137/202 |
| 5,090,443 A | * | 2/1992 | Jacobsen | 137/429 |
| 5,443,453 A | * | 8/1995 | Walker et al. | 604/248 |
| 5,464,388 A | * | 11/1995 | Merte et al. | 604/153 |
| 5,531,723 A | * | 7/1996 | Solazzo | 604/283 |
| 5,553,636 A | * | 9/1996 | Hoeptner, III et al. | 137/59 |
| 5,575,767 A | * | 11/1996 | Stevens | 604/53 |
| 5,665,074 A | * | 9/1997 | Kelly | 604/247 |
| 5,738,662 A | * | 4/1998 | Shannon et al. | 604/247 |
| 5,916,201 A | * | 6/1999 | Wilson, Jr. et al. | 604/248 |
| 5,988,201 A | * | 11/1999 | Lebkuchner et al. | 137/202 |
| 6,197,005 B1 | * | 3/2001 | Gerlach et al. | 604/247 |
| 6,302,137 B1 | * | 10/2001 | Devall | 137/202 |

* cited by examiner

Primary Examiner—Lesley D. Morris
Assistant Examiner—F. Nicolas
(74) Attorney, Agent, or Firm—Kenneth P. Glynn, Esq.

(57) ABSTRACT

The present invention is a continuous irrigation system for medical applications, including transurethral resection procedures, which provides automatic bag switching. It includes: (a) a first and second liquid irrigation bag; (b) a first proximal tubing and a second proximal tubing extending from the first liquid irrigation bag and the second liquid irrigation bag, respectively, and (c) a control valve device. The control valve device includes: (i) a main housing having a hollow body and a top and a bottom; (ii) an outlet located on and extending downwardly from the bottom for attachment of distal delivery tubing thereto; (iii) two inlets, located on or near the top of the main housing for the first and second proximal tubing; (iv) a floatation valve for opening and closing the second inlet. There is a distal delivery tubing connected to the outlet.

18 Claims, 4 Drawing Sheets

CONTINUOUS IRRIGATION Y-TUBING CONTROL VALVE DEVICE AND SYSTEM

BACKGROUND OF THE INVENTION

1. Field of the Invention

The present invention relates to continuous irrigation of patients in surgical situations, and particularly to irrigation systems and control valve devices used therein. The present invention control valve devices provide for automatic switching from a first liquid irrigant bag to a second, without the need for manual changing, valving or other operation.

2. Information Disclosure Statement

During the course of specialized operative procedures by endoscopic surgeons (urologists, orthopedic and gynecologic surgeons), the constant flow of irrigating solutions is mandatory and required to maintain clear visibility of the operative field. Any interruption of this flow causes blood and operative debris to obscure the field, temporarily. As a result, the resection or procedure must be terminated until the flow has been re-established. This irrigant, which may be water, normal saline, or sorbitol, or other aqueous solution, is usually delivered through a Y-tubing, two bags connected to the upper portions of the Y which join into a common tubing to which the instrument is connected. When one bag is empty, the nurse usually closes the valve at the base of the empty bag and opens the full bag's valve. She then removes the empty bag and reconnects a new full one. Occasionally, both bags will be left running open together but unfortunately when this is done, the bags will empty together and the same process of lack of irrigant occurs as well. The process of switching from bag to bag is a process that involves constant monitoring of the irrigant by the nurse to effect a constant flow. Unfortunately, in practice this does not happen efficiently, and oftentimes, the nurse is involved in some other operating room task that temporarily distracts her from this important function. She may only be reminded by the surgeon when he observes that his operative field of vision is obscure due to the lack of irrigant. It takes her several seconds to minutes to restore this flow depending upon her involvement with other sometimes critical tasks at hand. These may be precious, anxious, and sometimes dangerous moments for the surgeon and the patient.

The prior art systems using the Y-connection which require manual switching, also sometimes create secondary problems, such as air pockets, or bubbles, in the lines, and, of course, may take nurses away from other essential tasks when needed.

Notwithstanding the prior art, the present invention which is directed to overcoming the foregoing problems, is neither taught nor rendered obvious thereby.

SUMMARY OF THE INVENTION

The present invention is a system, and a device. The device is a continuous irrigation Y-tubing control valve for medical applications, including transurethral resection procedures. It includes (a) a main housing, the main housing having a hollow body and having a top and a bottom; (b) an outlet located on and extending downwardly from the bottom of the main housing for attachment of distal delivery tubing thereto for liquid flow to a patient; (c) two inlets, being a first inlet and a second inlet, located on the top of the main housing and extending upwardly therefrom for attachment of proximal tubing to each of the two inlets; (d) a hollow, sealed floatation valve hingedly attached to and located within the main housing. The valve has a first, open position and a second, closed position, wherein the first open position of said valve allows liquid flow from both the first inlet and the second inlet to the outlet, and wherein the second, closed position allows liquid flow from the first inlet to the outlet and prevents liquid flow from the second inlet to the outlet. Thus, when liquid flows while the floatation valve is in its first, open position, the main housing fills with liquid and the floatation valve rises to its second, closed position to permit flow only from the first inlet. On the other hand, when liquid flow from the first inlet ceases, the main housing empties and the floatation valve returns to an open position to permit flow from the second inlet to the outlet. The floatation valve is hingedly connected to the main housing in an offset manner so that it will maintain an open position by force of gravity when it does not contain enough liquid for floatation thereof. It will maintain a closed position via floatation when the main housing contains substantial liquid therein.

In some preferred embodiments, the top and the bottom of the main housing are separate pieces and are assembled together. The bottom includes sidewalls to establish a liquid holding hollow component or chamber, and the top is a cover component therefor. In one preferred embodiment, the top has downwardly extending brackets for hinged connection to the floatation valve. The floatation valve is a hollow, closed, floatable component and may advantageously be formed of molded plastic.

The valve device of may have a bottom with a generally semi-circular shape and the floatation valve may have a generally v-shape, such that when said floatation valve is in its open position, a bottom portion of the floatation valve rests on an inside surface of the main housing bottom.

The present invention continuous irrigation system may include:

(a) a first liquid irrigation bag;
(b) a second liquid irrigation bag;
(c) a first proximal tubing extending from the first liquid irrigation bag;
(d) a second proximal tubing extending from the second liquid irrigation bag;
(e) the control valve device described above; and,
(f) distal delivery tubing connected to the outlet for liquid flow to a patient via an instrument to which the tubing is connected at its opposite terminus.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figure 1A:
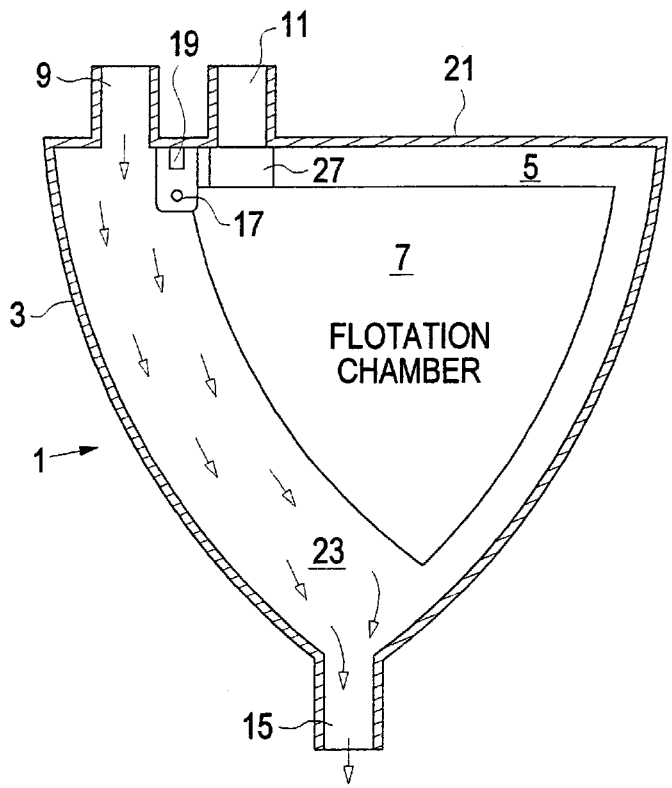
FIGS. 1a and 1b show one embodiment of a present invention valve device in its closed and open position, respectively.

The present invention system includes a Y-tubing which has two arms of the Y that are connected to two large irrigation bags or bottles and a single common delivery tube through which the irrigant is delivered to the operative instrument. The main controlling element is at the "Y" where a specially designed device responds when the first bag is empty and initiates flow from the second bag. This automatic switching Y-tubing assembly, i.e. this present invention system may include:

1) Two proximal tubes,
2) one control valve device with a floatation valve, and
3) one distal delivery tube.

Each of the proximal tubes are connected to irrigant bags or bottles delivering irrigant to the central floatation chamber. The irrigant is then delivered to the surgical instrument or Foley catheter for CBI (continuous bladder irrigation) via the distal delivery tube. Both proximal and distal tubing may be made of vinyl and fitted with appropriate connectors. The central floatation valve device has two inlet ports on or near the top e.g. at the top left side of the housing for delivery of irrigant from the first and second bags respectively.

In some preferred embodiments, the housing has curved lateral sides to decrease turbulent flow of irrigant within it, and has flat sides in the anterior-posterior walls. Within the main housing is a floatation valve which has its rotational axis, off center, e.g. on the left, and the free swing floatation valve, e.g., on the right. Close to the rotation axis is a valve top, or seal, which corresponds to the underside of the inlet port of the second bag which occludes it when the valve is in the raised position due to floatation caused by irrigant.

When the irrigant from both bags is started, the chamber or main housing fills with fluid, the floatation valve rises, occluding the outflow from one bag, conserving this bag as a reserve. As irrigant from the first bag is used, the main housing begins to empty and the floatation valve drops, allowing irrigant from the second bag to provide a constant continuous flow without interruption.

If there is a demand for both bags to run simultaneously (for better visibility in special situation), the delivery valve only needs to be opened more so that the chamber outlet port area is increased.

In some embodiments, in order for the floatation area to rise and fall at will, it is advantageous that air be allowed to enter and exit the floatation chamber. This may be done via a hydrophobic filter membrane, retaining and confining any irrigant within the chamber while air is evacuated. In preferred embodiments, this membrane, or air inlet, is unnecessary, as the device will function as desired without a separate air intake membrane. In order for the device to work properly in some embodiments, it is necessary that the inflow from the first bag (measured in cc/sec or cross-section area of the inflow port) be greater than the outflow port. This maintains the chamber filled to capacity until the first bag is empty.

Figure 1B:
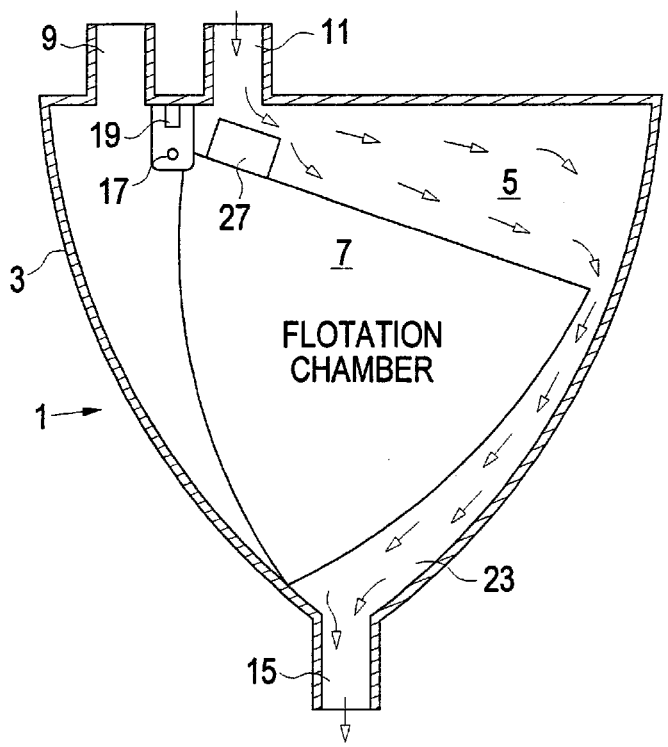

Referring now to FIGS. 1a and 1b, there is shown a present invention floatation valve device for irrigation control when two separate irrigation liquid bags are employed. As mentioned, this valve device 1 replaces the prior art Y-connectors used previously, and hence is itself a different type of Y-connectors (two lines in, one line out). Valve device 1 is preferably constructed of plastic, such as molded or cost plastic, but could be made of composite materials, stainless steel, glass, ceramic, cement or combinations thereof, without exceeding the scope of the present invention.

Valve device 1 not only replaces the prior art Y-connectors for better flow control to produce longer continuous flow without manual attention, but also provides for automatic switching from one bag to the other in a timely fashion, and eliminates the possibility of air bubbles or air pockets in the lines.

Thus, in FIGS. 1a and 1b, valve device 1 is shown in its closed and open position respectively. Identical parts in both Figures are identically numbered.

There is a main housing 3 which has a top 21, and a bottom 23. Top 21 includes a first inlet 9 for connection via tubing to a first irrigation liquid bag (not shown) and a second inlet 11 for connection via tubing to a second 10 irrigation liquid bag (also not shown).

Bottom 23 includes an outlet 23 for connection to a distal tube for patient treatment. Typically, such distal tubing is connected to a downstream device instrument for appropriate patient irrigation during surgery.

There is a floatation valve 7 which is hingedly connected to main housing 3 via hinge 17 and bracket 19. There is also a stop 27 for closing and opening flow from inlet 11.

Initially, liquid flows into main housing 3 from both inlets 9 and 11 and thus fills the main housing while fluid exits outlet 15. The fluid build up floats valve 7 to its closed position as shown in FIG. 1a, wherein stop 27 seals inlet 11, and then only liquid from inlet 9 runs as shown by the arrows in FIG. 1a. When the liquid from a bag connected to inlet 9 is emptied, liquid level in main housing 3 drops, valve 7 drops on its hinge 17 to the open position shown in FIG. 1b, and the liquid will flow from inlet 11 as shown in FIG. 1b. Air may flow in or out via 13 to prevent a partial vacuum or lock up.

Figure 2:
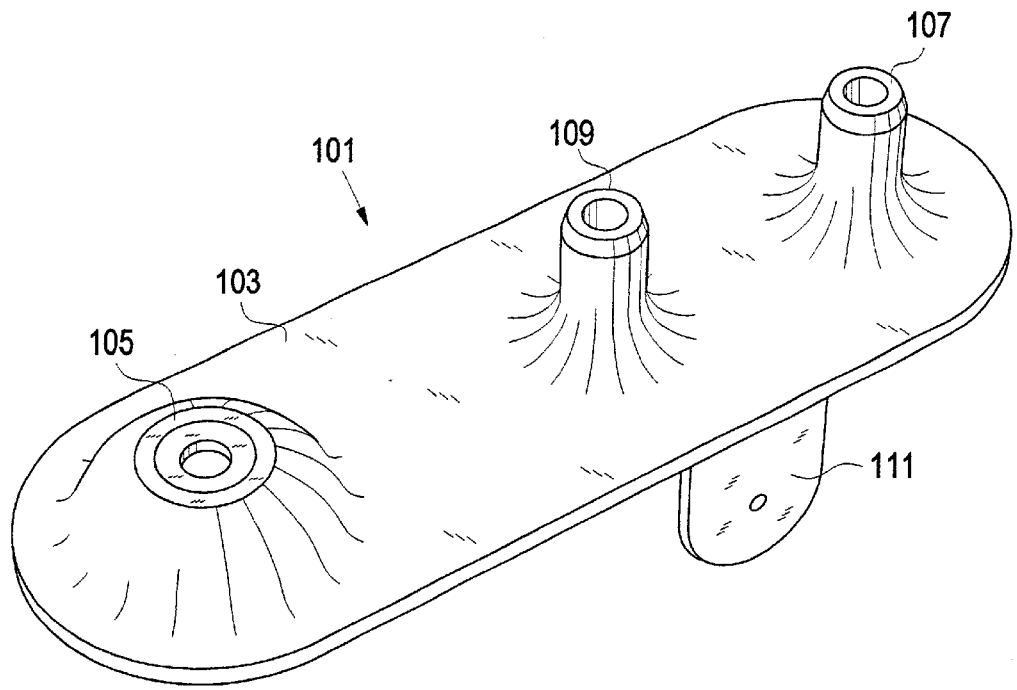
FIGS. 2, 3 and 4 illustrate a present invention top, a float valve and a valve device, respectively; and, FIG. 5 illustrates a present invention system.
Figure 3:
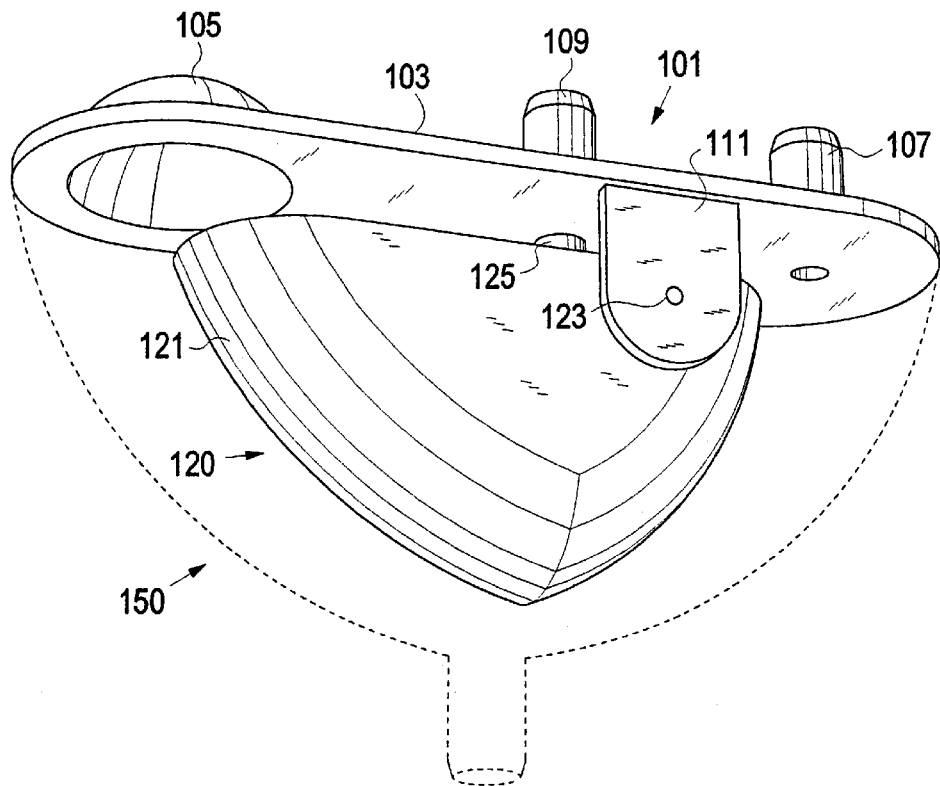
Figure 4:
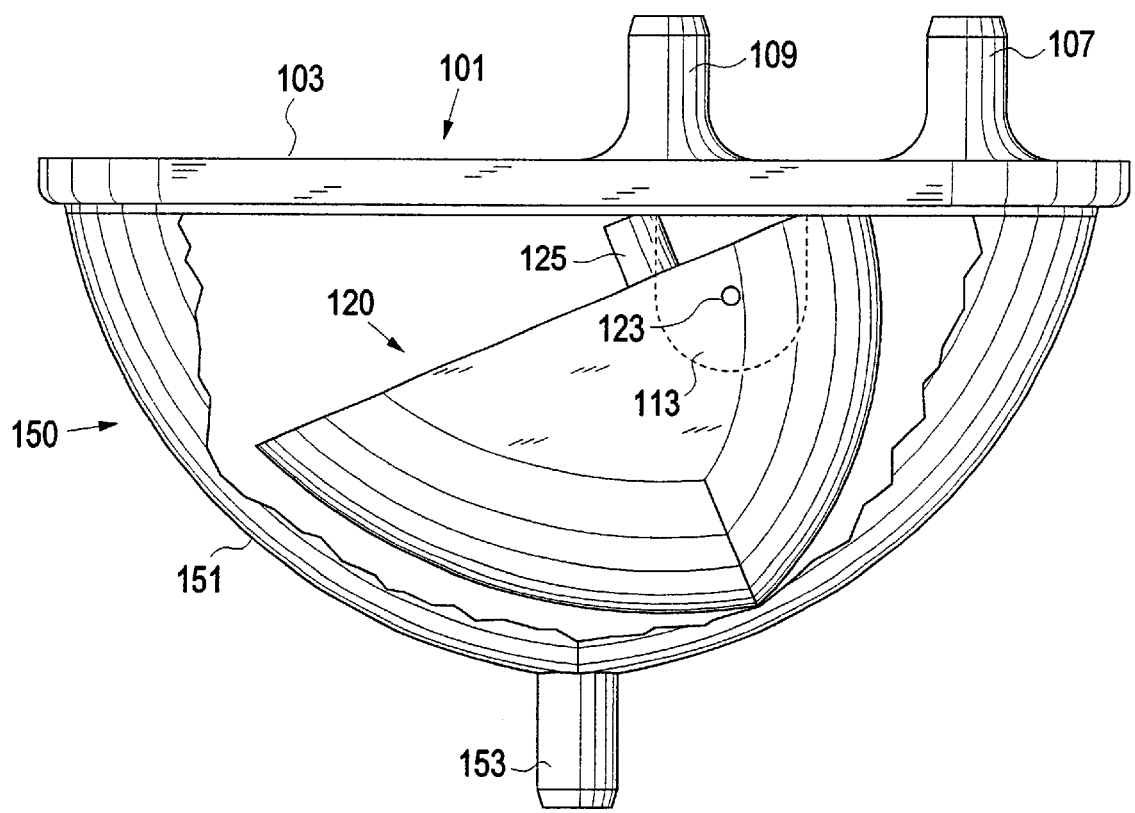

FIG. 2 shows a main housing top oblique view of an alternative embodiment present invention device and FIG. 3 shows a side perspective view of the FIG. 2 top with a floatation valve attached thereto. FIG. 4 shows a side cut view of a control valve device, including the main housing top of FIG. 2, the floatation valve of FIG. 3, and a main housing bottom. FIGS. 2, 3, and 4 will be described collectively, and identical components are identically numbered.

Main housing top 101 has a substantially flat panel 103, with a vent 105, a first inlet 107 and second inlet 109. It also includes a bracket 111 (and a second similar bracket, not shown) for hingedly mounting floatation valve 120 (FIGS. 3 and 4). Thus, bracket 111 (and its hidden opposite bracket) receives hinge pin 125 of floatation valve 120, which is part of and permits hinged rotation of floatation valve 120. Valve 120 also has a hollow, sealed V-shaped body 121, and an inlet seal 125 located in line with inlet 109 so that it seals inlet 109 when in its closed position, as shown in FIG. 3, to prevent flow into main housing 150.

As shown in FIG. 4, main housing 150 includes bottom 151 with outlet 153 and contains the floatation valve 120, shown here in the open position to permit flow from inlet 109.

Figure 5:
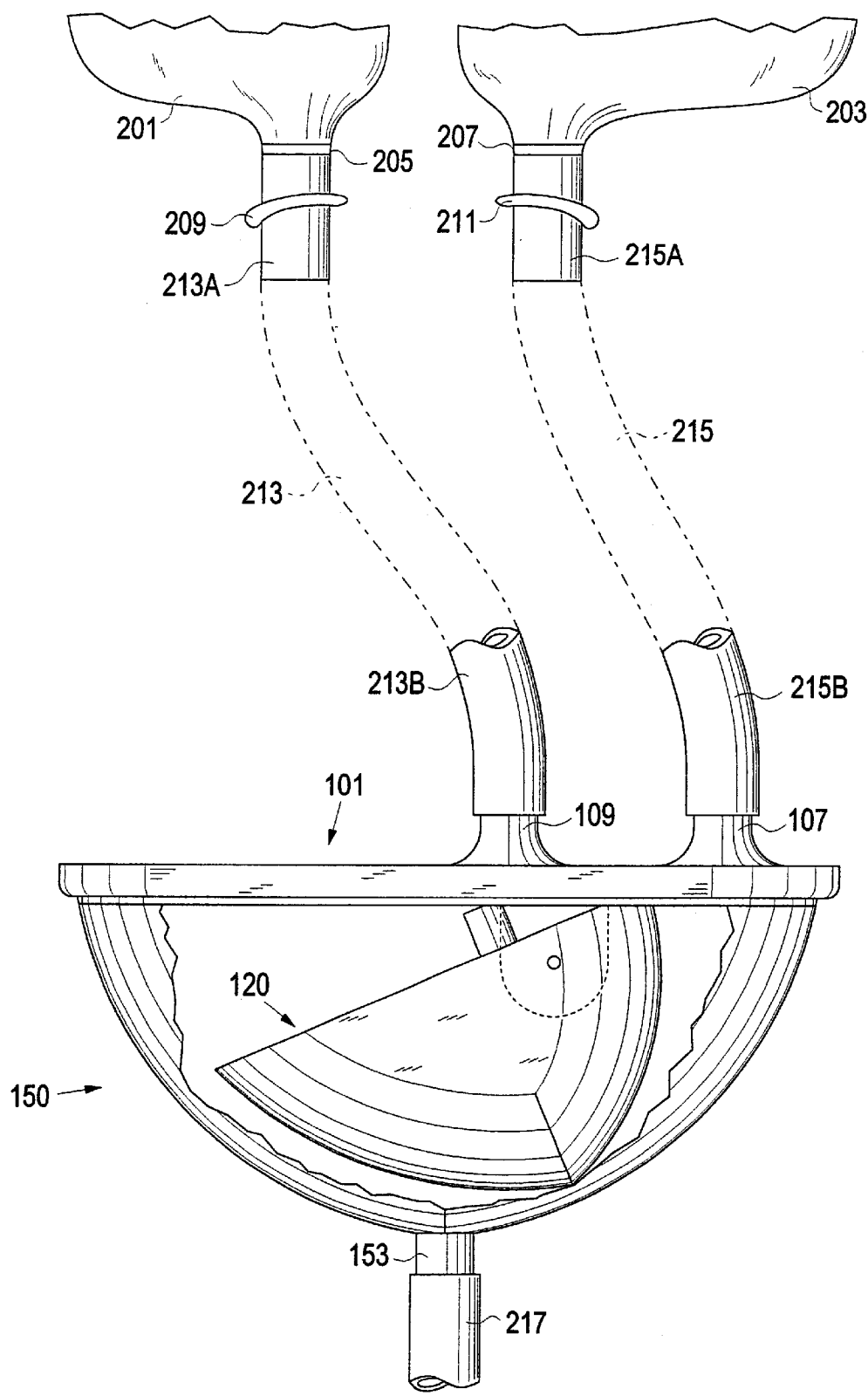

FIG. 5 shows a partial cut view of a present invention system and it includes main housing top 101, main housing bottom 150 and floatation valve 120 shown in FIG. 4. First inlet 107 is connected to tubing 215 which is shown in segment as 215b, with its upper portion 215a connected to irrigation bag 203 at connector 207. Pinch clamp 211 is also attached to the tubing. Similarly, tubing segment 213b is connected to irrigation bag 201 at connector 205. Pinch clamp 209 is also attached to the tubing, as shown. Main housing bottom 150 has outlet 153 connected to tubing 217 for delivery of irrigants to instruments for washing critical patient areas during surgery. The system shown in FIG. 5 functions as described above.

Obviously, numerous modifications and variations of the present invention are possible in light of the above teachings. It is therefore understood that within the scope of the appended claims, the invention may be practiced otherwise than as specifically described herein.

What is claimed is:

1. A continuous irrigation Y-tubing control valve device for medical applications, including transurethral resection procedures and other requirements demanding constant irrigation, which comprises:

(a) a main housing, said main housing having a hollow body and having a top and a bottom;

(b) an outlet located on and extending downwardly from said bottom of said main housing for attachment of distal delivery tubing thereto for liquid flow to a patient;

(c) two inlets, being a first inlet and a second inlet, located on the top of said main housing and extending upwardly therefrom for attachment of proximal tubing to each of said two inlets;

(d) a hollow, sealed floatation valve hingedly attached to and located within said main housing, said valve having a first, open position and having a second, closed position wherein said first open position of said valve allows liquid flow from both said first inlet and said second inlet to said outlet, and wherein said second, closed position allows liquid flow from said first inlet to said outlet and prevents liquid flow from second inlet to said outlet, such that when liquid flows while said floatation valve is in its first, open position, said main housing fills with liquid and said floatation valve rises to its second, closed position to permit flow only from said first inlet, and, when liquid flow from said first inlet ceases, said main housing empties and said floatation valve returns to an open position to permit flow from said second inlet to said outlet.

2. The valve device of claim 1 wherein said floatation valve is hingedly connected to said main housing in an offset manner so that it will maintain an open position by force of gravity when said main housing does not contain enough liquid for floatation thereof and will maintain a closed position via floatation when said main housing contains substantial liquid therein.

3. The valve device of claim 1 wherein said top and said bottom are separate pieces and are assembled together to form said main housing.

4. The valve device of claim 3 wherein said bottom includes sidewalls to establish a liquid holding hollow component and said top is a cover component therefor.

5. The valve device of claim 1 wherein said device is formed of molded plastic.

6. The valve device of claim 4 wherein said top has downwardly extending brackets for hinged connection to said flotation valve.

7. The valve device of claim 6 wherein said device is formed of molded plastic.

8. The valve device of claim 4 wherein said bottom has a generally semi-circular shape and said floatation valve has a generally v-shape, such that when said floatation valve is in its open position, a bottom portion of said floatation valve rests on an inside surface of said main housing bottom.

9. A continuous irrigation system for medical applications, including transurethral resection procedures, which comprises:

(a) a first liquid irrigation bag;

(b) a second liquid irrigation bag;

(c) a first proximal tubing extending from said first liquid irrigation bag;

(d) a second proximal tubing extending from said second liquid irrigation bag;

(e) a control valve device, which includes:

(i) a main housing, said main housing having a hollow body and having a top and a bottom;

(ii) an outlet located on and extending downwardly from said bottom of said main housing for attachment of distal delivery tubing thereto for liquid flow to a patient;

(iii) two inlets, being a first inlet and a second inlet, located on or near said top of said main housing and extending upwardly therefrom, said first inlet being attached to said first proximal tubing, and said second inlet being attached to said second proximal tubing;

(iv) a floatation valve hingedly attached to and located within said main housing, said valve having first, open position and having a second, closed position wherein said first, open position of said valve allows liquid flow from both said first inlet and said second inlet to said outlet, and wherein said second, closed position allows liquid flow from said first inlet to said outlet and prevents liquid flow from second inlet to said outlet, such that when liquid flows while said floatation valve is in its first, open position, said main housing fills with liquid and said floatation valve rises to its second, closed position to permit flow only from said first inlet, and, when liquid flow from said first inlet ceases, said main housing empties and said floatation valve returns to an open position to permit flow from said second inlet to said outlet; and, (f) distal delivery tubing connected to said outlet for liquid flow to a patient.

10. The system of claim 9 wherein said floatation valve is hingedly connected to said main housing in an offset manner so that it will maintain an open position by force of gravity when said main housing does not contain enough liquid for floatation thereof and will maintain a closed position via floatation when said main housing contains substantial liquid therein.

11. The system of claim 9 wherein said top and said bottom are separate pieces and are assembled together to form said main housing.

12. The system of claim 11 wherein said bottom includes sidewalls to establish a liquid holding hollow component and said top is a cover component therefor.

13. The system of claim 9 wherein said device is formed of molded plastic.

14. The system of claim 12 wherein said top has downwardly extending brackets for hinged connection to said floatation valve.

15. The system of claim 14 wherein said device is formed of molded plastic.

16. The system of claim 12 wherein said bottom has a generally semi-circular shape and said floatation valve has a generally v-shape, such that when said floatation valve is in its open position, a bottom portion of said floatation valve rests on an inside surface of said main housing bottom.

17. The system of claim 9 wherein said system further includes a first pinch clamp located on said first proximal tubing and a second pinch clamp located on said second proximal tubing.

18. The system of claim 9 wherein said first and second irrigation bags contain liquid selected from the group consisting of water and aqueous based irrigation solutions.

* * * * *